United States Patent [19]

Fritz et al.

[11] 4,352,689

[45] * Oct. 5, 1982

[54] METHOD FOR CONTROLLING APICAL DOMINANCE

[75] Inventors: Charles D. Fritz, Hatfield, Pa.; Wilbur F. Evans, Kuala Lumpur, Malaysia; Anson R. Cooke, Hatfield, Pa.

[73] Assignee: Union Carbide Corporation, Danbury, Conn.

[ * ] Notice: The portion of the term of this patent subsequent to Apr. 22, 1992, has been disclaimed.

[21] Appl. No.: 221,817

[22] Filed: Jan. 28, 1972

Related U.S. Application Data

[60] Division of Ser. No. 869,386, Oct. 24, 1969, which is a continuation-in-part of Ser. No. 693,698, Dec. 27, 1967, abandoned, which is a continuation-in-part of Ser. No. 617,860, Feb. 23, 1967, abandoned.

[51] Int. Cl.$^3$ ............................................. A01N 57/00
[52] U.S. Cl. ........................................ 71/86; 71/71; 71/76
[58] Field of Search ............................................ 71/86

Primary Examiner—Glennon H. Hollrah
Attorney, Agent, or Firm—Robert C. Brown

[57] ABSTRACT

A method for controlling apical dominance which comprises applying to the plant an effective amount, ranging between about 0.1 lb. and about 16 lbs. per acre of plants being treated, of 2-chloroethylphosphonic acid.

1 Claim, No Drawings

METHOD FOR CONTROLLING APICAL DOMINANCE

This invention relates to the use of 2-chloroethylphosphonic acid in order to control apical dominance and this is a division of application Ser. No. 869,386, filed Oct. 24, 1969 and entitled "Growth Regulation Process", which in turn was a Continuation-In-Part application based on prior co-pending application Ser. No. 693,698, filed Dec. 27, 1967 and entitled "Phosphonic Compound Growth Regulation Process", now abandoned, which in turn was a Continuation-In-Part application based on prior co-pending application Ser. No. 617,860, filed Feb. 23, 1967 and entitled "Growth Regulation Process Utilizing Phosphonic Compounds", now abandoned.

The induction of an ethylene response in plant growth by other means has been known for some time in the art. See "Plant Biochemistry" by James Bonner and J. E. Varner (1965), pages 641 to 664.

A fairly well known ethylene response is the use of gaseous ethylene in the ripening of bananas which has been carried out on a commercial scale for many years. It is also known to employ ethylene in essentially gaseous form to stimulate flower initiation in pineapples. See "Hormonal Control of Plant Growth" by N. S. Parihar (1964), pages 69 to 79. Here, ethylene was applied on a commercial scale using cumbersome equipment to drench the pineapple plants with ethylene-saturated liquid. Similar, but less powerful effects on plant tissues have been caused by other unsaturated hydrocarbic gases.

The mechanism by which ethylene and the other gases affect the growth cycle of plants is far from fully understood, but it is clear that they do play a role. It will be seen that the phosphonic acid compound used to practice the present invention contains in its structure molecular configurations which are capable of breaking down into ethylene or like compounds, although there is no intention to limit the present invention to this theory or any other theory.

The use of certain other phosphonate compounds in the agricultural art is known for herbicidal purposes as set forth in U.S. Pat. Nos. 2,927,014 and 3,223,514. However, it will be seen that the compounds disclosed in the aforesaid two patents do not produce the growth regulating responses for ethylene-type response of the present invention.

Instead, the present invention involves controlling apical dominance through the application of 2-chloroethylphosphonic acid at the plant site.

Reference is hereby made to the following prior co-pending applications, the disclosures of which are hereby incorporated by reference:

(1) Application Ser. No. 617,860; Filed: Feb. 23, 1967; Inventors: Charles D. Fritz and Wilbur F. Evans; Title: Growth Regulation Process Utilizing Phosphonic Compounds.

(2) Applications Ser. Nos. 617,820 and 617,819; Both Filed: Feb. 23, 1967; Inventor: David I. Randall; Title of Both: Phosphonic Acid Esters and Method for Their Preparation; Assignee: General Aniline and Film Corporation.

The foregoing applications specified hereinabove disclose preparation techniques for 2-chloroethylphosphonic acid.

Certain preliminary details connected with the controlling of apical dominance should make for a better appreciation of the invention.

Control of apical dominance can be produced on a variety of plant species when they are treated with 2-chloroethylphosphonic acid, including privet (*Ligustrum ovalifolium*), blueberry (*Vaccinum corymbosum*), azalea (*Rhododendron obtusum*), soybeans (*Glycine mas.*), snapbeans (*Phaseolus vulgaris*), tomatoes (*Lycopersicon esculentum*), alligator weed (*Alternanthua philoxeroides*) and monocotyledons such as rice (*Oryza sativa*), johnsongrass (*Sorghum halopense*) and wild oats (*Avena fatua*). This type of response can also be of value in the control of roadside grasses. It has been suggested that the removal of the lead bud (e.g. by pinching) should allow growth of auxiliary buds; but it is generally found that on removal of the lead bud one of the auxiliary buds takes over the activity and dominance of the lead bud. The use of 2-chloroethylphosphonic acid, however, usually retards the activity of the lead bud for a while but then later restores the lead bud to normal growth, with production of normal flowers and normal fruit; and thus one avoids the permanent loss of buds inevitably associated with pinching. However, some plant species respond differently when treated with 2-chloroethylphoshonic acid for control of apical dominance—growth inhibition may extend to include not only the lead bud but also lateral buds along the stem. Examples of such plants are tobacco (*Nicotiana tabacum*) and chrysanthemum (*Chrysanthemum* sp.)—this type of response is useful for preventing sucker growth from lateral buds on tobacco.

2-chloroethylphosphonic acid used in the method of the present invention is soluble in water and can be applied to plants in aqueous solutions composed wholly or partially of water. Partial solutions include those formed of water and, for instance, acetone, or methyl ethyl ketone. Any liquid medium may be used, provided that it is not toxic to the plant.

As will be demonstrated in connection with certain examples in this specification, 2-chloroethylphosphonic acid of the present invention has been quite effective in controlling apical dominance in connection with a wide variety of plant species at various concentrations of active phosphonic acid compounds. Amounts of as little as 0.1 lb./acre of 2-chloroethylphosphonic acid have been observed to cause marked increase in branching and lateral growth of several varieties of tomato plants. Moreover, compounds used in the process of this invention, when employed at concentrations ranging from 0.1 lb. to 16 lbs./acre (or from 10 to 48,000 p.p.m.) have demonstrated pronounced control of apical dominance.

The precise amount of 2-chloroethylphosphonic acid will depend upon the particular plant species being treated. An amount of from about 0.1 lb. to as much as 25 lbs. to 30 lbs./acre of these compounds, when applied to plants, will result in varying control of apical dominance, depending upon the total amount of compound used, as well as the particular plant species which is being treated. Of course, the amount of 2-chloroethylphosphonic acid should be non-phytotoxic with respect to the plant being treated.

It is preferred that the compound used in the process of the present invention be applied at rates of ½ to 4 lbs./acre in aqueous solution and that the application rate in terms of total volume varies from about 1 to 100 gallons per acre.

The 2-chloroethylphosphonic acid used in the process of this invention is generally soluble in water. However, if desired, the compound used in the process of this invention may be absorbed onto solid carriers such as vermiculite, attaclay, talc and the like for application via a granular vehicle. Application of water thin solutions or solids is accomplished using conventional equipment that is well known in the art.

Although the preferred method of application of the compound used in the process of this invention is directly to the foliage and stems of plants, it has been found that the compound may be applied to the soil in which the plants are growing, and that such compound will be root-absorbed to a sufficient extent so as to result in controlling apical dominance in accordance with the teachings of this invention.

The compound used in the process of the present invention is preferably applied to growing plants as set forth in the example in this specification.

The compound which is usable in the process of the present invention may be prepared in accordance with said previously mentioned application Ser. No. 617,820 entitled "Phosphonic Acid Esters and the Method for Their Preparation", the entire disclosure of which is hereby incorporated by reference, as applicable to 2-chloroethylphosphonic acid.

In order to illustrate the surprising results flowing from this invention, there are presented below a series of experimental test results which are presented solely by way of illustration and are in no way intended to be construed as in any way limiting the scope of this invention.

It has been theorized that with the practice of the present invention the 2-chloroethylphosphonic acid breaks down outside the plant while still in the aqueous solution in which it was applied, and that the ethylene thus released is assimilated by the plant in gaseous form. However, this seems unlikely since even when stabilized against hydrolytic breakdown, the phosphonic acid will, to a greater or lesser extent, exert plant growth regulating activity when applied to plants, as demonstrated, for instance, by the epinasty tests upon tomato plants.

It is therefore theorized that the phosphonic acid used in the practice of the present invention exerts its control of apical dominance, at least in the great majority of cases, by assimilation into the metabolic system of the plant. Indeed, analytical investigations have shown that immediately following application to the plant, residues of the phosphonic acid are for a limited period of time to be found in plant tissues. Other investigations have shown that in many plants some time after the application of the phosphonic acid, the plant tissues contain detectable amounts of ethylene.

From the foregoing, it can be concluded that the phosphonic acid is broken down within plant tissue to release ethylene, and that the ethylene thus released exerts its normal functions. Indeed, it appears that the amount of ethylene released within the plant tissue is greater than that which could be derived from the phosphonic acid assimilated by the plant tissues. If this is correct, then it would seem to follow that the assimilation of the phosphonic acid by the plant tissues may trigger-off the enzymatic or other systems within the plant which, in themselves, generate ethylene.

The foregoing explanation is presented in an effort to promote a better understanding of the present invention, but since other investigations are still being carried out, it is quite possible that additional observations may necessitate a revision or even an abandonment of such a theory. In recognition of this, it is again repeated that the reasons why the present invention has proved to be so successful have not as yet been determined with certainty, and this specification is to be so understood.

The following evaluation demonstrates the use of the compound of the method of the present invention for removal of apical dominance:

EXAMPLE 1

Peanut (*Arachis hypogaea*) plants were sprayed during the period of vegetative growth prior to flowering with aqueous solutions of 2-chloroethylphosphonic acid. The results are recorded below:

| Treatment rate ppm | % Removal of apical dominance |
|---|---|
| Control | 0 |
| 250 | 35 |
| 500 | 48 |
| 1000 | 75 |

Removal of apical dominance is of economic value for control of plant growth. Pod weight or yield is often correlated positively with the number of primary and secondary branches developed prior to flower initiation.

Other examples are set forth in application Ser. Nos. 869,386, 693,698 and 617,860, specified hereinabove, with such other examples relating to controlling apical dominance being incorporated herein.

Without further elaboration, the foregoing will so fully illustrate our invention that others may, by applying current or future knowledge, readily adopt the same for use under various conditions of service.

What is claimed as the invention is:

1. A method for controlling apical dominance which comprises applying to the plant an effective amount, ranging between about 0.1 lb. and about 16 lbs. per acre of plants being treated, of 2-chloroethylphosphonic acid.

* * * * *